United States Patent [19]

Stancesco et al.

[11] Patent Number: 4,959,212
[45] Date of Patent: Sep. 25, 1990

[54] OXIDIZING-ENERGIZING COMPOSITION AND METHOD FOR THE TREATMENT OF DIABETES

[76] Inventors: Alexandra Stancesco, 1184 Main St., Apt. 75, River Edge, N.J. 07661; Apostol Spiliadis, 5-D Patton Dr., Bloomfield, N.J. 07003; Theodore Dumas, 977 Waterloo Street, Ontario, London, Canada, N 6 A 2 x 4

[21] Appl. No.: 209,877

[22] Filed: Jun. 22, 1988

[51] Int. Cl.$^5$ ..................... A61K 37/62; A61K 31/52; A61K 31/505
[52] U.S. Cl. .................... 424/94.1; 424/94.2; 424/94.4; 424/94.5; 514/44; 514/45; 514/46; 514/47; 514/48; 514/49; 514/50; 514/51; 514/52; 514/866
[58] Field of Search .............. 424/94.1, 94.2, 94.4, 424/94.5; 514/44, 45, 46, 47, 48, 49, 50, 51, 52, 866

[56] References Cited

U.S. PATENT DOCUMENTS

| | | | |
|---|---|---|---|
| 3,426,125 | 2/1969 | Shigeta et al. | 424/94.1 |
| 4,308,257 | 12/1981 | Caspe | 514/47 |
| 4,544,550 | 10/1985 | Rodolfo | 514/866 |
| 9,609,914 | 6/1910 | Heinemann | 424/94.4 |

OTHER PUBLICATIONS

Biochemistry, A. L. Lehninger, 2 ed, 1975, Worth Publishers, New York, pp. 423–426.
Reddi, A. "Riboflavin Nutritional Status & Flavoprotein Enzymes in Streptozotocin-Diabetic Rats", BA82(7):65812, 1986.

*Primary Examiner*—Jacqueline Stone
*Assistant Examiner*—Jean C. Witz
*Attorney, Agent, or Firm*—Richard N. Miller

[57] ABSTRACT

A non-toxic, oxidizing-energizing composition suitable for use as an accelerator of the carbohydrate oxidative degradation metabolic process or the direct oxidation of glucose which consists essentially of, by weight, (A) 10% to 95% of flavine-adenine dinucloeotide coenzyme (FAD) and (B) 10% to 95% of at least one coenzyme or enzyme selected from the group consisting of flavine mononucleotide coenzyme (FM), ubiquinone coenzyme (UBQ), uridine 5'-triphosphate coenzyme (UTP), triphosphopyridine nucleotide coenzyme (TPN), diphosphopyridine nucleotide coenzyme (DPN), adenosine triphosphate coenzyme (ATP), uridine diphosphate glucose coenzyme (UDPG), guanosine 5'-triphosphate coenzyme (GTP), glucose oxidase enzyme (GOD) and mixtures thereof; and (C) 0% to less than 50% of an enzyme selected from the group consisting of fructosediphosphate aldolase, phosphofructokinase, hexokinase, glucokinase, glucose 6-phosphate dehydrogenase, glucose phosphate isomerase, d-glucose-phosphotransferase and mixtures thereof, said composition being effective to reduce the blood glucose concentration in a human body afflicted with diabetes. A further aspect of the invention comprises the combination of 1 mg. to 100 mg. of the foregoing oxidizing-energizing composition with a daily dosage of an antidiabetic drug in an amount effective to lower the blood glucose concentration in the human body, said combination yielding a blood glucose concentration which is lower than the concentration produced by the antidiabetic drug alone as well as a method of lowering the blood glucose concentration in the human body comprising the step of administering the oxidizing-energizing composition in combination with the daily dosage of an antidiabetic drug.

21 Claims, No Drawings

OXIDIZING-ENERGIZING COMPOSITION AND METHOD FOR THE TREATMENT OF DIABETES

FIELD OF THE INVENTION

This invention relates to an oxidizing-energizing composition comprising a mixture of an isoalloxazine derived coenzyme—flavine-adenine dinucleotide (FAD)—and at least one other specific coenzyme or enzyme which is effective for accelerating the carbohydrate oxidative degradation metabolic process or for direct oxidation of glucose. The active groups of the components of the composition are the isoalloxazinic group, the pyrimidine-quinonic ring, the benzo-para-quinonic group, the pyridinic group and the energy-rich phosphate bonds. More particularly, it relates to an improved composition for reducing the blood glucose concentration in the human body consisting essentially of said oxidizing-energizing composition in combination with an antidiabetic drug in an amount effective to lower the blood glucose concentration. Also included is an improved method of lowering the blood glucose concentration in the human body comprising the step of administering said oxidizing-energizing composition in combination with the step of administering the daily dosage of an antidiabetic drug in an amount sufficient to lower the blood glucose concentration.

BACKGROUND AND PRIOR ART

Coenzymes and enzymes are non-toxic compounds which are naturally present in the human body. For example, it is known from the article in the Journal of Biological Chemistry, 223, page 569 (1956) by DeLuca and Kaplan and from the review by A. Holmgren in Experientia, 36 (Supplement), pages 149-180 (1980) that the coenzyme—flavine adenine dinucleotide (FAD)—plays an important part in the respiratory cycle of the red blood cells. Also, it is known from "Understanding Enzymes" (1981) by Trevor Palmer and a review entitled "The Pyridine Nucleotide Coenzymes" at pages 603-639 of Biological Oxidations (1968) edited by T. Singer that the coenzymes triphosphopyridine nucleotide (TPN or NADP) and diphosphopyridine nucleotide (DPN or NAD) act as a hydrogen carrier in anaerobic or aerobic oxidations and fermentations. Further, the article by Hall and Khorana in the Journal of the American Chemical Society, 76, page 5056 (1954) describes studies of the structure, the properties and the enzymatical preparation of the coenzyme uridine 5'-triphosphate (UTP) from uridine diphosphate (UDP). Additionally, the structure of the coenzyme flavine mononucleotide (FMN) is disclosed in U.S. Pat. Nos. 2,535,385; 2,610,178-9; 2,740,775 and 3,118,876. Similarly, it has been recognized in "Biomedical and Clinical Aspects of Coenzyme Q," volumes 1-5, by K. Folkers et al. that ubiquinone (UBQ) has an important function in the body due to its involvement in electron transport, i.e., in the oxidation of succinate or the reduced form of diphosphonucleotide, and is a factor in human congestive heart failure, hypertension, host defense and prevention of cardiotoxicity. The investigations of urine specimens from patients having Diabetes Mellitus have not shown any correlation between the urinary excretion of UBQ and the state of diabetic control according to the article in the Archives of Biochemistry and Biophysics, 95, page 348 (1961) by S. S. Bergen et al. "Nucleotides and Coenzymes" (1964) by D. Hutchinson discloses at pages 36-82 that uridine diphosphate glucose (UDPG) catalyzes the conversion of galactose-1-phosphate to glucose-1-phosphate in the human body. Finally, "The Enzymes," volume 7, pages 567-586 (1963) by P. D. Boyer et al. discloses the structure and properties of glucose oxidase enzyme (GOD).

From an energy standpoint, there is an equilibrium between endoergic and exoergic reactions in a healthy human body without diabetes. Normally, the energy supplied by the energy producing reactions is capable of providing a good reaction speed for the entire carbohydrate degradation cycle and, thus, the body has the capacity for normal consumption of carbohydrates upon the expected normal, internal release by the pancreas of secreted insulin as needed. On the other hand, a diabetic body is characterized principally by the decrease in the number of "active" insulin secreting centers in the pancreas, thereby resulting in a smaller amount of insulin available for the degradation of carbohydrates. Also, the reaction speed of the degradation cycle is slower and the blood glucose concentration tends to vary within wide limits—reaching especially high levels during the first 2-4 hours after eating. Therefore, the existence of diabetes has serious consequences on the normal functioning of the body.

At the present time diabetes may be treated either by sulfonamidic drugs or by insulin injection. When administered, the sulfonamidic drugs work by over stimulating the secretion of pancreas active centers and attempt to reequilibrate the insulin balance. However, the speed of the entire metabolic cycle is not totally restored, but is only improved. Furthermore, with continued administration, the deterioration of the pancreas active islets usually increases and either stronger sulfonamidic drugs or higher dosages of such drugs are required. Finally, fewer pancreas active islets must secrete more and more insulin with the result that the breakdown of the active centers increases and eventually injection of insulin is required. Use of injected insulin typically has the disadvantage of causing large variations in blood glucose concentrations—usually reaching dangerously high levels of prolonged duration.

The new oxidizing energizing compositions which are the subject of this invention provide a new way of overcoming the foregoing problems. For example, it is believed that the inventive compositions are effective to accelerate the carbohydrate degradation metabolic cycle or to oxidize glucose directly in the bodies of humans who exhibit only a minor deficiency in secretion of insulin. In this manner, the need to resort to antidiabetic drugs may be postponed for a long time if the patient follows the dietary regimen. Additionally, in those humans already ingesting antidiabetic drugs, small amounts of the inventive compositions taken in conjunction with an antidiabetic drug are effective to provide lower concentrations of blood glucose than are achieved using the antibiabetic drug alone, thereby permitting either a reduction in the dosage of the drug and/or an increase in the daily intake of carbohydrates and/or total removal of the drug. In any event, the reduction in pancreas stimulation usually arrests the further progression of the disease. Such results are surprising in view of the fact that the inventive compositions consist essentially of added amounts of compounds already present in the human body.

SUMMARY OF THE INVENTION

Generally, the described invention relates to a non-toxic, oxidizing-energizing composition suitable for use as an accelerator of the carbohydrate oxidative degradation metabolic process or of the direct oxidation of glucose which consists essentially of, by weight, (A) 10% to 95% of flavine-adenine dinucleotide coenzyme (FAD) and (B) 5% to 90% of at least one coenzyme or enzyme selected from the group consisting of flavine mononucleotide coenzyme (FMN), ubiquinone coenzyme (UBQ), uridine 5'- triphosphate coenzyme (UTP) triphosphopyridine nucleotide coenzyme (TPN), diphosphopyridine nucleotide coenzyme (DPN), adenosine triphosphate coenzyme (ATP), uridine diphosphate glucose coenzyme (UDPG), guanosine 5'- triphosphate coenzyme (GTP), glucose oxidase enzyme (GOD) and mixtures thereof; and, optionally, (C) 0% to less than 50% of an enzyme selected from the group consisting of fructosediphosphate aldolase, phosphofructokinase, hexokinase, glucokinase, glucose 6-phosphate dehydrogenase, glucose phosphate isomerase, d-glucose-phosphotransferase and mixtures thereof, said composition being effective to reduce the blood glucose concentration in a human body afflicted with diabetes. A further aspect of the invention resides in the use of 1 mg. to 100 mg. per day of the inventive oxidizing-energizing composition in combination with a daily dosage of an antidiabetic drug in an amount effective to lower the blood glucose concentration in the human body, said combination Yielding a blood glucose concentration which is lower than the blood glucose concentration produced by the antidiabetic drug alone.

In its more preferred aspect, the inventive oxidizing-energizing composition consists essentially of, by weight, 10% to 95% of FAD coenzyme and a second component selected from the group consisting of at least one of 5% to 40% of UTP coenzyme, 5% to 70% of TPN coenzyme, 5% to 20% of UDPG coenzyme, 5% to 80% UBQ coenzyme and 20% to 90% of GOD enzyme. For example, satisfactory blood glucose controlling compositions include the following: 20% to 30% FAD, 20% to 40% UBQ, 20% to 40% UTP and 10% to 15% UDPG; 70% to 90% FAD, 5% to 20% UBQ and 5% to 15% UTP; and 10% to 40% FAD and 60% to 90% GOD. Most preferably, the inventive oxidizing-energizing composition consists essentially of, by weight, either 60% to 90% of FAD, 5% to 25% of TPN and 5% to 15% of UTP or 10% to 30% of FAD, 15% to 30% of TPN and 40% to 70% of GOD or 10% to 30% FAD and 70% to 90% GOD.

When the oxidizing-energizing composition is used in combination with an antidiabetic drug in an amount of the drug which is effective to lower the blood glucose concentration in the body, it is preferred that the blood glucose lowering drug be a sulfonamide derivative. Most preferably, the inventive composition will be used in conjunction with a daily dosage of either 1.25–20 mg. of glyburide—1-[(p-(5-chloro-o-anisamido) ethyl) phenyl)-sulfonyl] 3-cyclohexylurea—sold under the registered trademark Micronase ® or 125–750 mg. of chlorpropamide—1-((p-chlorophenyl)-sulfonyl) 3-propylurea—sold under the trademark Diabinese ®.

Also within the scope of the described invention is the improved method of lowering the blood glucose concentration in the human body comprising the step of administering 1–100 mg. per day of the subject oxidizing-energizing composition in conjunction with the administration of the daily dosage of a blood glucose lowering drug in an amount effective to lower the blood glucose concentration in the human body. In practice, the oxidizing-energizing composition will be administered at approximately the same time as the blood glucose lowering drug, wither immediately before or immediately after the drug. Preferably, when the daily dosage of the antidiabetic or blood glucose lowering drug is administered in other than a single dose, it is preferred that a portion of the oxidizing-energizing composition accompany each does of the drug, with the proportion of said composition at each use corresponding to the proportion of the daily requirement of the drug being taken at that time. Most preferably, the inventive composition is administered just prior to the administration of the drug or insulin. In its most preferred aspects, the most preferred oxidizing-energizing composition is administered in conjunction with either two dosages comprising the daily requirement of Micronase ® or three dosages comprising the daily requirement of Diabinese ®. Optimally, the inventive oxidizing energizing composition is formulated as part of the antidiabetic drug and, thus, is administered simultaneously with the drug.

DETAILED DESCRIPTION OF THE INVENTION

Each of the essential components of the inventive oxidizing energizing composition whether a coenzyme or an enzyme is non-toxic and is present in a healthy human body. Furthermore, each component has been used for other purposes, including biochemical studies and as a food supplement in many cases.

The essential flavine adenine dinucleotide coenzyme (FAD) is chemically identified as riboflavine 5'-(trihydrogen diphosphate) 5',5'-ester with adenosine or isoalloxazine-adenine-dinucleotide and its structural formula is as follows:

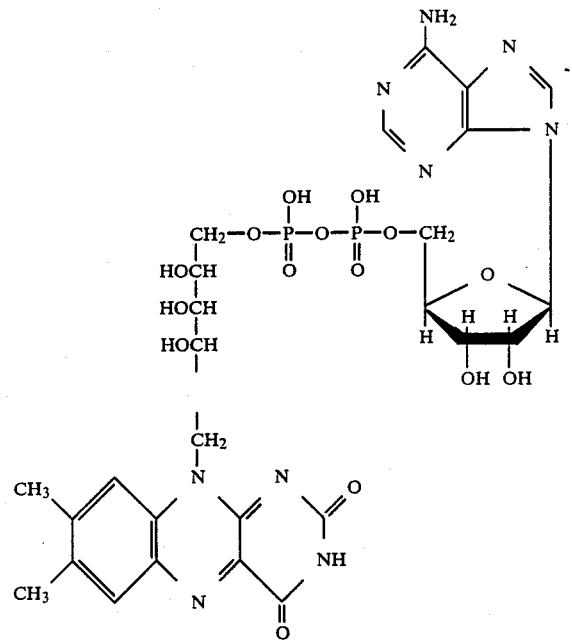

It is described in paragraph 4013 of the Merck Index, Tenth edition, and in Volume 2 of "The Enzymes" (1960) edited by P. Boyer et al. This coenzyme has a pyrimidine-quinonic structure derived from the cyclic system of benzopteridine (isoalloxazine) and has been isolated from yeast, liver, kidney, heart and muscles. The essential active group of FAD in the oxido-reductive process is the alloxazinic group. FAD is available commercially from Sigma Chemical Company in St. Louis, Mo., in the form of a powder containing 94–99% by weight of a water-soluble disodium salt. One commercial FAD product contains a small amount, i.e., less than 1% by weight, of another enzyme, catalase, which is effective to remove hydrogen peroxide.

FAD is the prosthetic group of certain flavoproteins including glucose oxidase enzyme (GOD). FAD has the capacity to transfer hydrogen directly to molecular oxygen via the enzymatic system of cytochromes and, therefore, it is a very important factor for the acceleration of the respiratory cycle. In the oxidation of a substrate such as D-glucose, the reduced form of FAD, namely FADH2, and d-glucono-delta-lactone are formed. The reduced form of FAD may further react with oxygen to yield hydrogen peroxide and to regenerate FAD. Additional FAD and other coenzymes or enzyme from the oxidizing energizing composition are essential because the FAD and other coenzyme or enzyme existing in the body are inhibited in their action by the reaction products such as glucono-lactone. Thus, by daily ingestion of additional FAD and other coenzyme or enzyme, e.g., GOD, an additional cycle of the aforementioned oxido-reductive reaction is created, which is not dependent upon the FAD and GOD naturally existing in the body.

The identity of the second component (B) in the oxidizing-energizing composition is selected from the group of the coenzymes and enzyme which follow:

1. Flavine mononucleotide coenzyme (FMN) is chemically identified as riboflavine 5'-phosphate sodium. Its structural formula follows:

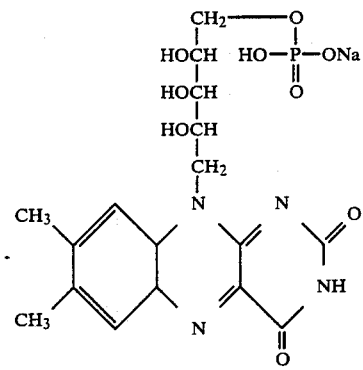

It is described in Paragraph 8100 of the Merck Index, Tenth edition, and in the aforementioned U.S. patents. This coenzyme has been used as a food supplement; and it is available commercially from Sigma Chemical Company in the form of a powder having an active concentration of 99% by weight as the water-soluble disodium salt of FMN.

2. Ubiquinone coenzymes, also known as coenzyme Q, are based on the 2,3-dimethoxy-5-methyl-para-benzoquinone nucleus with a variable terpenoid side chain containing 1 to 12 mono-unsaturated trans-isoprenoid units, with ten units being most common. According to a dual system of nomenclature, the compounds are described as coenzyme Qn wherein n is an integer from 1 to 12 or ubiquinone(x) wherein x designates the total number of carbons in the side chain. The structural formula of ubiquinones follows:

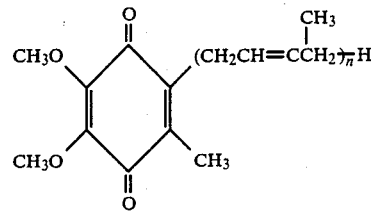

$n = 1-12$

Ubiquinone (50) is identified as coenzyme Q10. Ubiquinones occur in the majority of aerobic organisms and naturally occurring members are coenzymes Q6 –Q10. These compounds also have been prepared synthetically. Such compounds are described in paragraph 9641 of the Merck Index, Tenth edition, as well as in a series of books entitled "Biomedical and Clinical Aspects of Coenzyme Q" by K. Folkers et al. Q10 has been used as a food supplement and it is available commercially from Sigma Chemical Company as a powder from bovine heart, with a 90–95% active concentration of ubiquinone by weight. Q10, as a para-benzoquinonic derivative, probably has a tendency to yield the quinhydronic form from 1 mole of the quinonic form and 1 mole of the hydroquinonic form. Because the quinhydronic form is less reactive than each of the other forms, it is speculated that this form is the cause of the apparent inactivity of Q10 in some of our experiments wherein other oxidizing components were absent.

3. Uridine 5'-triphosphate coenzyme (UTP) is chemically identified as uridine 5'-(tetrahydrogen triphosphate). Its structural formula follows:

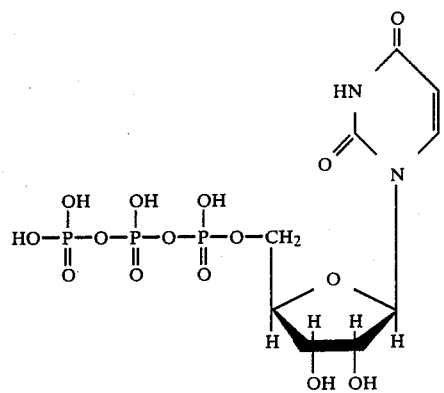

UTP is a dihydroxypyrimidine (uracyl) derivative analog of adenosine 5'-triphosphoric acid coenzyme (ATP). It has been isolated from rabbit muscle and it also can be obtained by synthesis. It is disclosed in paragraph 9688 of the Merck Index, Tenth edition. It is available commercially from Sigma Chemical Company as a water-soluble powder derived from yeast having an active concentration of 97–99% coenzyme by weight. It is believed that this coenzyme accelerates the phosphorylation phase of the metabolic carbohydrate degradation process.

4. Triphosphopyridine nucleotide coenzyme (TPN) is chemically identified as nicotinamide adenine dinucleotide phosphate (coenzyme II). Its structural formula follows:

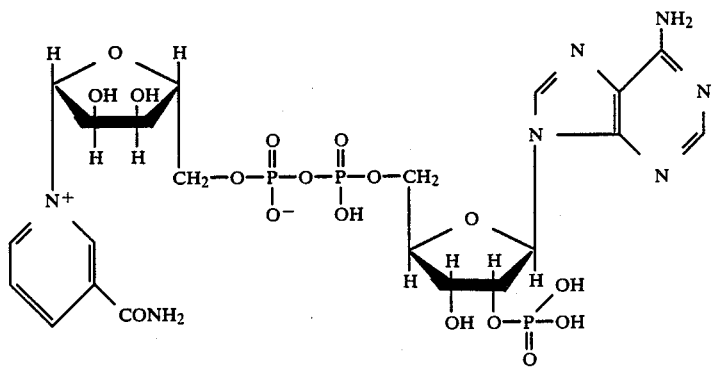

It is disclosed in paragraph 6197 of the Merck Index, Tenth edition, and it has been isolated from horse blood, hog liver and sheep liver. It can be obtained by synthesis, too. It acts as a hydrogen carrier in anaerobic and aerobic oxidation and the active group in the oxidation reduction process is the amidopyridinic group. This coenzyme has been used in biochemical studies. It is available commercially from Sigma Chemical Company as a dry powder having an active concentration of 98–100 % by weight of a water-soluble sodium salt of the coenzyme. TPN functions as a dehydrogenating agent in the metabolic carbohydrate degradation process and is used together with FAD because the reduced TPNH form is unable to transfer its hydrogen directly to molecular oxygen in the absence of FAD.

5. Diphosphopyridine nucleotide coenzyme (DPN) is chemically identified as adenosine 5'-(trihydrogen diphosphate)-5',5'-ester with 3-(aminocarbonyl)-1-B-D-ribofuranosyl-pyridinium hydroxide, inner salt, or Coenzyme I or nicotinamide-adenine dinucleotide (AND). Its structural formula follows:

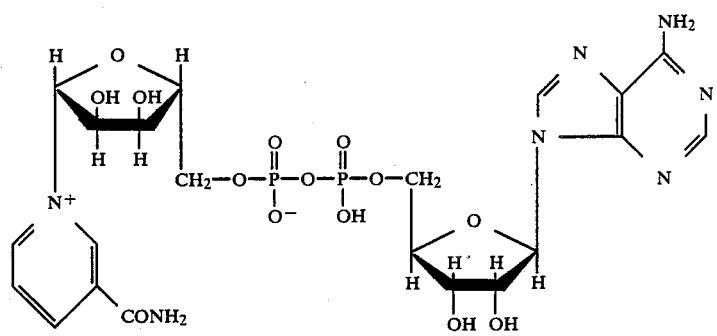

The active group of this coenzyme in the metabolic oxidation-reduction process is the amido-pyridinic group—the same as for TPN. The difference between DPN and TPN is the presence of one more phosphoric group in TPN. This coenzyme is disclosed in paragraph 6194 of the Merck Index, Tenth edition. It has been isolated from baker's yeast, from rabbit muscle and from erythrocytes and it can be synthesized, too. It is used usually for the alcoholic fermentation of glucose and it is available commercially from Sigma Chemical Company as a dry powder having an active concentration of 90% by weight as a water-soluble sodium salt of the coenzyme.

6. Adenosine 5'-triphosphate coenzyme (ATP) is chemically identified as adenosine 5'-(tetrahydrogen triphosphate). It is used in the phosphorylation phase of the carbohydrate degradation process. Its structural formula follows:

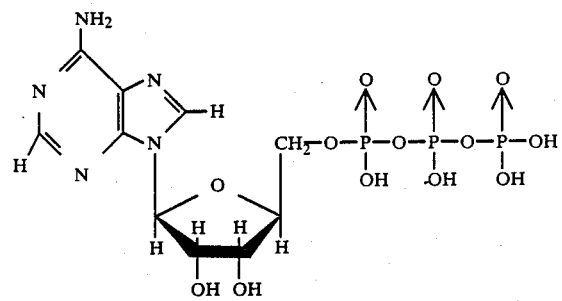

It is disclosed in paragraph 146 of the Merck Index, Tenth edition and at pages 3–38 of "The Enzymes" Vol. 2A (1960) by P. D. Boyer et al. It has been iosolated from rabbit muscle and it may be prepared synthetically. ATP is characterized by a content of phosphate bonds which are rich in energy. It is available commercially from Sigma Chemical Company as a dry powder having an active concentration of 99% by weight as the water-soluble disodium salt of the coenzyme. The disodium salt exhibits limited stability in water and is not stable in the presence of some impurities, such as vanadium. These instability problems limit its use in the inventive compositions.

7. Uridine glucose coenzyme (UDPG) is chemically identified as uridine 5'-(trihydrogen diphosphate) mono-2-D-glucopyranosyl ester or cogalactoisomeraze. Its structural formula follows:

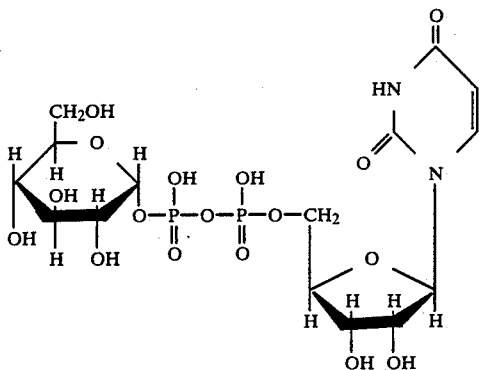

It is disclosed in paragraph 9687 of the Marck Index, Tenth edition and in "The Enzymes," Vol. 2A (1960) by P. D. Boyer et al. It has been isolated from baker's yeast and is present in animal tissue. Also, it can be prepared by synthesis. This coenzyme has been used in biochemical studies. It is available commercially from Sigma Chemical Company in the form of a dry powder containing 98-100% by weight as a water-soluble sodium salt of the coenzyme. UDPG catalyzes the conversion of galactose-1-phosphate into glucose-1-phosphate, said product being the first to appear in the metabolic process upon hydrolysis of glycogen.

9. Glucose oxidase enzyme (GOD) is chemically identified as β-D-glucopyranose aerodehydrogenase. It is disclosed in the Enzyme Handbook, Vol. I (1969) by T. E. Barman according to the Enzyme Code as EC 1.1.3.4. Additionally, it is disclosed in paragraph 4320 of the Merck Index, Tenth edition. It is an enzyme obtained from mycelia of fungi such as Aspergilli and Penicillia. It is a flavoprotein and catalyzes the oxidation of glucose to gluconic acid, the molecular oxygen being reduced to hydrogen peroxide. Commercial preparations frequently contain appreciable amounts of another enzyme, catalase, which is desirable where removal of hydrogen peroxide is desired. A glucose oxidase unit is defined as that quantity of enzyme which will oxidize 1 millimole of B-D-glucose to D-gluconic acid and hydrogen peroxide per minute at pH 5.1 and 35° C. In the presence of excess oxygen, the activity may increase 50–100%. The molecular weight of the product obtained from Aspergillus Niger is about 186,000. This enzyme is highly specific for B-D-glucose. It has been used in the protection of food, to remove glucose from egg albumen and to remove oxygen from canned foods. It is available from Sigma Chemical Company in the form of a dry, water-soluble powder which contains 100,000 to 150,000 units of enzyme per gram of powder and about 80% by weight of protein. The commercial enzyme used in the inventive compositions contains trace amounts of amylase, maltase, glycogenase and galactose oxidase.

The proportions of each of the coenzymes or enzyme used as component B in conjunction with FAD is variable within the range of 5% to 90% by weight because the proportion of each is dependent upon the inhibiting capacity of the total coenzyme or enzyme concentration—the sum of the naturally occuring concentration and the added concentration in the body—, the stability of the coenzyme or enzyme in the body and the interaction between the coenzymes or enzymes present in the body. Generally, the proportion, by weight, of the coenzyme or enzyme used in combination with FAD is as follows: 20% to 50% of FMN; 5% to 80% of UBQ; 5% to 40% of UTP; 5% to 70% of TPN; 50% to 80% of ATP; 5% to 20% of UDPG; 25% to 45% of GTP; 5% to 60% DPN; and 20% to 90% of GOD. Often component B of the oxidizing-energizing composition will consist of at least two of the members of the group. ATP is a lesser preferred coenzyme because of its instability problems and DPN is less preferred as a dehydrogenating agent than TPN because TPN appears to be more specific for the enzymes used in the aerobic degradation of carbohydrates in persons afflicted with diabetes.

With the exception of the preferred compositions containing a mixture of 10% to 30% by weight of FAD coenzyme and 70% to 90% by weight of GOD, the other preferred compositions contain two or more members of group B compounds in combination with FAD. Other preferred compositions follow, with the proportions being by weight:

60% to 90% FAD; 5% to 25% TPN; 5% to 15% UTP;

10% TO 30% FAD; 15% TO 30% TPN; 40% to 70% GOD;

30% to 70% FAD; 20% to 60% UBQ; 10% to 25% UTP; and

30% to 50% FAD; 15% to 30% FMN; 20% to 40% UBQ; 10% to 20% UTP.

The first two compositions in the foregoing list are the most preferred along with the mixtures of FAD and GOD. The next two compositions in the list are highly preferred, particularly where the dietary fortifying properties of UBQ are desired.

In addition to the above-described essential ingredients or components, optionally the oxidizing-energizing compositions may include a minor proportion, i.e., generally from 0% to less than 50% by weight and preferably 0% to 25% by weight, of an enzyme selected from the group consisting of fructose diphosphate aldolase, phosphofructokinase, hexokinase, glucokinase, glucose 6-phosphate dehydrogenase, glucose phosphate isomerase, D-glucose phosphotransferase and mixtures thereof. Each of these enzymes is known to exist in the normal human body and to play a part in one or more of the reactions which characterize the metabolic oxidative degradation of carbohydrates in the human body. Thus, under certain conditions, added amounts of one or more of these enzymes may be included in the oxidizing-energizing compositions to further accelerate the carbohydrate oxidative degradation process or the direct oxidation of glucose. When included in the inventive oxidizing-energizing composition, the proportion of the essential components will be reduced by an amount equivalent to the amount of the added optional enzyme.

Each of the optional enzyme components usually is present in the normal human body and each has been used in the biochemical study of the metabolic process. A description of each of the optional enzyme components follows:

1. Fructosediphosphate aldolase enzyme is chemically identified as fructose-1,6-diphosphate D-glyceraldehyde-3-phosphate lyase. This enzyme is disclosed at pages 736-737 of "Enzyme Handbook," Vol. II (1969) by T. E. Barman according to the Enzyme Code (EC=4.1.2.13). This enzyme is obtained from yeast and has an approximate molecular weight of about 70,000. This enzyme specifically catalyzes the reaction wherein fructose-1,6-diphosphate is split into dihydroxy acetone phosphate and D-glyceraldehyde 3-phosphate.

2. Phosphofructokinase enzyme is chemically identified as ATP:D-fructose-6-phosphate 1-phosphotransferase. It is disclosed at pages 386-387 of "Enzyme Handbook," Vol. I (1969) by T. E. Barman according to the Enzyme Code (EC=2.7.1.11). This enzyme has been isolated from yeast, rabbit muscle and sheep heart and the enzyme obtained from rabbit muscle has a molecular weight of about 360,000. This enzyme in combination with ATP or UTP facilitates the phosphorylation of D-fructose-6-phosphate to D-fructose-1,6-diphosphate in the carbohydrate oxidation process.

3. Hexokinase enzyme is chemically identified as ATP:D-hexose-6-phosphotransferase. It is disclosed at pages 377-378 of "Enzyme Handbook," Vol. I (1969) by T. E. Barman according to the Enzyme Code (EC=2.7.1.1. The enzyme is obtained from yeast and rat liver and the molecular weight of the material isolated from yeast is about 99,000. This enzyme in combination with ATP coenzyme facilitates the phosphorylation of D-hexose, D-glucose, D-mannose, D-glucosamine or D-galactose in the metabolism of carbohydrates by the human body.

4. Glucokinase enzyme is chemically identified as ATP:D-glucose 6-phosphotransferase. It is disclosed at pages 379-380 of "Enzyme Handbook," Vol. I (1969) by T. E. Barman according to the Enzyme Code (EC=2.7.1.2). This enzyme is isolated from rat liver and has an approximate molecular weight of about 50,000. In combination with ATP it is effective in the phosphorylation of d-glucose.

5. Glucose 6-phosphate dehydrogenase is disclosed at pages 73-74 of "Enzyme Handbook," Vol. I (1969) by T. E. Barman according to the Enzyme Code (EC=1.1.1.49). It has been isolated from human erythrocyte, yeast and rat mammary gland and the molecular weight ranges from 63,000 to 190,000 depending upon the source of the enzyme. In combination with TPN or DPN, this enzyme facilitates the reaction of the coenzyme with D-glucose 6-phosphate to yield the reduced form of the coenzyme and D-glucono- -lactone 6-phosphate.

6. Glucose phosphate isomerase is chemically identified as D-glucose-6-phosphate ketol-isomerase. It has been isolated from brewer's yeast (m.w.=145,000) and bovine mammary gland (m.w.=48,000 or 125,000). This enzyme is disclosed at pages 837-838 of "Enzyme Handbook," Vol. II (1969) by T. E. Barman according to the Enzyme Code (EC=5.3.1.9). In the process of metabolizing carbohydrates, it facilitates isomerization of D-glucose-6-phosphate to D-fructose-6-phosphate.

7. D-glucose phosphotransferase (EC=2.7.1.h) is disclosed at page 426 of "Enzyme Handbook," Vol. I by T. E. Barman according to the Enzyme Code (EC=2.7.1.h). It has been isolated from aerobacter aerogenes and mycobacterium smegmatis. In the metabolic carbohydrate degradation process, it facilitates the transfer of the 1-phosphate group of D-glucose-1-phosphate to the six position of D-glucose-6-phosphate.

Generally, the foregoing optional enzymes are important in the formation of phosphate compounds or in the rearrangement of phosphate compounds in the carbohydrate degradation process. Because the functions of each enzyme are quite specific, the optional enzyme components may be used in admixture with one another in order to achieve a desired result. However, when present in the oxidizing-energizing composition, the resultant composition will be effective to reduce the blood glucose concentration in a human body afflicted with some form of diabetes.

While the oxidizing-energizing compositions can be compounded in the form of a capsule or tablet, such compositions can be prepared in situ by adding the individual components to a non-toxic, edible carrier such as water or bread. In fact, in the following examples, the individual coenzymes or enzyme is added to water.

When the oxidizing-energizing compositions are employed in combination with an effective amount of an antidiabetic drug capable of lowering the blood glucose concentration used as a daily dose, the antidiabetic drug generally will be selected from the group consisting of glyburide, chlorpropamide, tolbutamide and tolazamide. Generally, the daily dosages of such antidiabetic drugs will be in the following ranges: 1.25 to 20 mg. of glyburide (Micronase ®); 125 to 750 mg. of chlorpropamide (Diabinese ®); 250 to 1250 mg of tolbutamide (Orinase ®); and 250 to 1250 mg. of tolazamide (Tolinase ®). The described drug dosages may be taken at one time—usually in the morning—or divided throughout the day—usually prior to each of the first three meals. Normally, when the drug dosage is divided, the dosage of the oxidizing-energizing composition also will be divided similarly in a proportion matching the proportion of the antidiabetic drug. Generally, the daily dosage of the oxidizing-energizing composition will range from 1 to 100 mgs., preferably from 5 to 35-40 mgs., per day, with the optimum being about 10 to 25 mgs. per day.

As indicated heretofore, the oxidizing-energizing composition may be used in humans to either reduce or to remove totally the daily drug dosage or to increase daily carbohydrate intake. Either action is significant from a medical standpoint and, therefore, the use of the combination of the oxidizing-energizing composition with an antidiabetic drug or ingested alone is considered to represent a significant advance in medical science.

Because the inventive oxidizing-energizing composition appears to potentiate the effects of insulin in lowering blood glucose concentrations, it is believed that such compositions also are useful in non-diabetic humans as well as mildly diabetic humans having diabetes problems which are controlled by diet alone as well as insulin dependent diabetic humans. More specifically, it is believed that the inventive composition when ingested alone co-acts with the insulin normally present in the body to reduce blood glucose concentrations by direct oxidation of glucose or by increasing the speed of the entire metabolic carbohydrate degradation process and by maintaining the insulin in its R-S-S-R active cysteinic form as opposed to the R-SH cysteine form which is inactive. Thus, it is considered that the oxidizing-energizing compositions are useful as a food supplement simply because they potentiate and enhance the effectiveness of the insulin present in the non-diabetic human body.

In another aspect, the invention resides in an improved method of lowering blood glucose concentrations in the human body comprising the step of administering from 1 to 100 mgs. of the inventive oxidizing-energizing composition described above in conjunction with the step of administering either insulin or an antidiabetic drug in an amount effective to stimulate insulin secretion in the human body on a daily basis. In the step of administering the inventive oxidizing-energizing composition, said composition may be administered before, simultaneously with or subsequent to the step of administering the insulin or antidiabetic drug. Furthermore, the daily dosage of the inventive composition may be administered either in a single dosage, preferably before the breakfast meal in the morning, or in divided doses, i.e., twice daily or three times daily, preferably before each meal. Additionally, said composition may be administered in the form of a preformed capsule or tablet or it may be distributed in a non-toxic, compatible, edible carrier, e.g., water or bread, or it may be administered in pre-formulated form with the drug itself. Preferably, the inventive composition will be administered prior to the step of administering the insulin or antidiabetic drug, although for practical purposes the steps will take place almost simultaneously. Most preferably, the oxidizing-erergizing composition will be preformulated as part of the drug and the steps will take place simultaneously.

This invention is illustrated further in the Examples which follow. All proportions in the examples and elsewhere in the specification are expressed on a weight basis unless otherwise stated. Additionally, the examples are given by way of illustration only and the invention is not limited to the compositions and methods exemplified.

EXAMPLE 1

In Example 1, the blood glucose concentrations of a non-insulin dependent male diagnosed as having Diabetes Mellitus type II and receiving a daily dosage of 10 mg. of glyburide antidiabetic drug in the form of Micronase ® are measured for a period of four weeks in the presence of 5 mg. of an oxidizing-energizing composition comprising, by weight, 70% FAD, 20% TPN and 10% UTP. The subject weighs about 75 kg. and the carbohydrate values ingested per day are controlled in the range from 115-125 grams per day based upon the "Calories Control" regimen from the University of Pennsylvania Hospital. The Micronase ® is administered as follows: 5 mg. at 6:45 a.m. and 5 mg. at 5 p.m. The oxidizing-energizing composition is administered in water as a carrier and one half of the daily dosage is given at 6:45 a.m. and the other half of the dosage at 5 p.m. Blood glucose concentrations are determined in milligrams per deciliter (mg./dl) using Accu-Chek BG Monitor Test strips. A Lancet is used to prick the finger and blood glucose determinations are made before breakfast at 6:45 a.m. (BBK), before lunch at 12 noon (BL), before first dinner at 5:00 p.m. (B2D) and before the second dinner at 9:00 p.m. (B2D). The results are set forth in Table 1 below with the readings being described by a range. Blood glucose values are included for the same subject based upon a base period of 6 to 8 weeks when no oxidizing energizing composition is administered in order to provide a reference value.

TABLE 1

| Ex. | Micronase ®/ OEC mg./mg./day | Blood Glucose Value (mg./dl.) | | | |
|---|---|---|---|---|---|
| | | BBK | BL | B1D | B2D |
| Comp 1 | 10/0 | 140-166 | 165-225 | 170-240 | 160-220 |
| 1 | 10/5 | 106-115 | 125-152 | 108-125 | 102-130 |

Table 1 clearly shows that the ingestion of 5 mg. per day of the oxidizing energizing composition significantly reduced the blood glucose concentrations when used in conjunction with a 10 mg. per day dosage of glyburide antidiabetic drug. For purposes of comparison, the blood glucose value for a normal, non-diabetic adult generally is in the range of 80-120 mg./dl.

EXAMPLES 2 and 3

Example 1 is repeated with the exceptions that the carbohydrate value ingested is increased to 180-190 grams per day—a 54% increase in caloric intake—in Example 2 and to 200-210 grams per day—a 71% increase in caloric intake—in Example 3 and the oxidizing energizing composition is increased to 10 mg. per day in Example 2 and to 20 mg. per day in Example 3. Table 2 sets forth the resultant blood glucose values.

TABLE 2

| Ex. | Micronase ®/OEC mg./mg./day | Blood Glucose Value (mg./dl.) | | | |
|---|---|---|---|---|---|
| | | BBK | BL | B1D | B2D |
| 2 | 10/10 | 85-110 | 120-135 | 86-112 | 75-115 |
| 3 | 10/20 | 92-97 | 115-118 | 103-112 | 98-109 |

The results in Table 2 show that concentrations of 10 mg. and 20 mg. of the oxidizing energizing composition yield lower blood glucose concentrations at increased levels of carbohydrate ingestion. Further, these results show a more significant reduction in blood glucose concentration is achieved as the concentration of oxidizing energizing composition is increased from 5 mg. per day to 10 mg. per day as compared with an increase from 10 mg. per day to 20 mg. per day. While the blood glucose values achieved in Examples 2 and 3 are very good, it should be recognized that the blood glucose values do vary with the type of diabetes. For example, where the type of diabetes causes the blood glucose values to be higher, lower values may be achieved either by slightly reducing carbohydrate intake or by further increasing the amount of the oxidizing-energizing composition (OEC) or by employing a different OEC.

EXAMPLES 4 and 5

Example 3 is repeated with the exceptions that the daily dosage of antidiabetic drug is decreased to 7.5 mg. per day and to 5 mg. per day respectively and blood glucose concentrations are monitored for one week. Results are shown in Table 3.

TABLE 3

| Ex. | Micronase ®/ OEC mg./mg./day | Blood Glucose Value (mg./dl.) | | | |
|---|---|---|---|---|---|
| | | BBK | BL | B1D | B2D |
| 4 | 7.5/20 | 120-135 | 130-148 | 132-145 | 137-148 |
| 5 | 5/20 | 142-154 | 150-165 | 165-172 | 175-192 |

The results in Table 3 clearly show that use of the oxidizing-energizing composition in conjunction with the antidiabetic drug enables the subject to reduce the daily dosage of the drug. For example, the blood glucose values for Example 5—5 mg. per day of drug at a carbohydrate intake of 200-210 grams per day— are similar to those obtained in the comparative in Example 1 wherein 10 mg. of drug is employed at a carbohydrate ingestion value of 115-125 grams per day—a reduction of more than 40% in caloric intake.

EXAMPLE 6

Example 1 is repeated with the exception that the oxidizing energizing composition comprises, by weight, 20% of FAD, 70% of TPN and 10% of UTP. Blood glucose values in mg./dl. for the four week period follow: BBK-115-128; BL-138-172; B1D-125-142; AND B2D-118-145. These values are about 10% higher than the values for the composition of Example 1. These results suggest that increasing the proportion of FAD in the oxidizing-energizing composition makes it more effective in reducing the blood glucose concentration.

Equivalent results may be achieved when ATP is substituted for UTP in the composition of Example 6. Furthermore, satisfactory blood glucose results are obtained when the composition of Example 6 includes 20% by weight of either hexokinase enzyme or phosphofructokinase enzyme and the other components are reduced by 20% each.

EXAMPLES 7, 8 and 9

Example 3 is repeated with the following exceptions: the carbohydrate ingestion value is 180-190 grams per day in Examples 7 and 8 and 150-170 grams/day in Example 9; and the oxidizing- energizing composition comprises, by weight, 60% FAD;, 20% TPN and 20% GOD in Example 7, 20% FAD, 20% TPN and 60% GOD in Example 8 and 10% FAD, 10% TPN and 80% GOD in Example 9. The proportions of Micronase R/OEC in mg./mg./day is 10/20 in Examples 7 and 8 and 5/35 in Example 9. The resultant blood glucose values for Examples 7-9 are set forth in Table 4.

TABLE 4

| Ex. | Micronase ®/ OEC mg./mg./day | Blood Glucose Value (mg./dl.) | | | |
|---|---|---|---|---|---|
| | | BBK | BL | B1D | B2D |
| 7 | 10/20 | 105-115 | 128-142 | 125-142 | 128-145 |
| 8 | 10/20 | 102-112 | 118-128 | 108-118 | 105-120 |
| 9 | 5/35 | 102-117 | 115-132 | 88-112 | 140-155 |

The results in Table 4 illustrate several important points. First, the oxidizing-energizing compositions of Examples 7 and 8 which consist of a mixture of FAD, TPN and GOD are effective to produce good controlled blood glucose concentrations. Furthermore, the results obtained with examples 7 and 8 show that better control is achieved when 40% by weight of GOD is substituted for a like proportion of FAD. Additionally, example 9 indicates that the OEC composition consisting of the FAD, The GOD produces good blood glucose values in the presence of only mg./day of Micronase ®.

While the blood glucose values in example 8 are not as low as those in example 3 wherein the OEC composition is a mixture of FAD, TPN and UTP and is present in a proportion of 20 mg./day, the results in example 9 are better than those noted Example 5 wherein the proportion of Micronase ® is 5 mg./day. Although the reasons for the foregoing results are not understood, it is believed that one reason is that the OEC compositions containing a major proportion of the mixture of FAD and GOD reinforces the proportions of those coenzymes in the body and enhances the direct oxidation of glucose. Thus, the OEC composition works independently of the normal metabolic carbohydrate degradation process and avoids the inhibition effects which may result from the OEC compositions of Examples and 3 which enhance the reactions in the metabolic carbohydrate degradation process. For this reason, it is considered that the OEC compositions comprising FAD and GOD or FAD, TPN and GOD or FAD, GOD and other enzymes or coenzymes are equal in effectiveness to the OEC compositions of Examples 2 and 3 in controlling blood glucose concentrations because the difference in actual blood glucose values are not statistically significant. In fact, increased concentrations of the OEC compositions containing a major proportion of FAD and GOD, e.g. 35, 40 or 50 mg./day, may be more effective based upon the results in example 5.

It is believed that another reason for the difference in the results noted in examples 9 and 5 is that the effectiveness of the OEC compositions containing a major proportion of FAD and GOD is independent of the concentration of insulin. Thus, for persons afflicted with a milder diabetes, e.g., one controlled with 250 mg./day of Diabinase ®, it is believed that 25-45 mg./day of an OEC composition containing a major proportion of FAD and GOD will be effective to control the blood glucose concentration in the absence of an anti-diabetic drug which stimulates insulin secretion.

When a minor proportion of TPN is included in an OEC composition containing a major proportion of FAD and GOD, it is believed that a very good composition is achieved for controlling blood glucose concentrations in the body: In addition to appearing to enhance the direct oxidation of glucose as described above, it is believed that such compositions also enhance the metabolic carbohydrate degradation process due to the dehydrogenating capability of TPN and the capability of FAD to reoxidize TPNH back to TPN.

EXAMPLE 10

Example 8 is repeated with the exceptions that the ratio of the oxidizing-energizing composition is reduced to 10 mg./day and the daily carbohydrate ingestion value is reduced to 140-160 grams per day. These changes yield blood glucose concentrations in mg./dl as follows: BBK-110-122, B1-124 -138, B1D-132-147 and B2D-134-150.

Tests of this type were made to avid the blood glucose values obtained in Examples 2, 3, 7 and 8 because such values may be too low to be bearable by all patients, at least at the beginning of the treatment or for patients who have a high oxygen concentration in the blood due to increased reaction speed caused by intense physical effort. These higher blood glucose values which may be satisfactory for many patients may be obtained using 10-20 mg./day of OEC composition and, optionally, an increased amount of carbohydrates ingested daily.

EXAMPLE 11

Example 3 is repeated with the exception that 750 mg./day of chlorpropamide in the form of Diabinase ® tablets is used as the antidiabetic drug. The carbohydrate ingestion value is 115-125 mg./day for Diabinase ® used alone and 180-190 grams per day for the combination of said drug and the oxidizing-energizing composition. The blood glucose concentrations are set forth in Table 5.

TABLE 5

| Ex. | Diabinese ® /OEC mg./mg./day | Blood Glucose Value (mg./dl.) | | | |
|---|---|---|---|---|---|
| | | BBK | BL | B1D | B2D |
| Comp | 750/0 | 205-235 | 245-280 | 235-275 | 265-285 |
| 10 | 750/20 | 100-120 | 125-145 | 115-130 | 130-150 |

The results of Table 5 show, as it is known, that Diabinese ® is less effective than Micronase ® in controlling blood glucose concentrations in the absence of the oxidizing energizing composition. Additionally, the results show that the oxidizing-energizing composition is effective with both antidiabetic drugs in reducing high blood glucose levels.

EXAMPLES 12 AND 13

Examples 2 and 3 are repeated with the exception that the oxidizing energizing composition comprises, by weight, 70% FAD, 20% Ubiquinone (50) as Q 10 and 10% UTP. Blood glucose concentrations obtained over a period of four weeks are set forth in Table 6.

TABLE 6

| Ex. | Micronase ®/ OEC mg./mg./day | Blood Glucose Value (mg./dl.) | | | |
|---|---|---|---|---|---|
| | | BBK | BL | B1D | B2D |
| 11 | 10/10 | 85–110 | 120–135 | 86–112 | 75–115 |
| 12 | 10/20 | 92–97 | 115–118 | 103–112 | 98–109 |

The results in Table 6 show that substitution of UBQ for TPN in the oxidizing energizing compositions of Examples 2 and 3 provides equally good blood glucose values after a test period of at least four weeks.

Despite the good results achieved with the compositions containing UBQ in Examples 12 and 13, it is believed that these compositions do not belong in the most preferred group of OEC compositions. More specifically, it noted that UBQ is not an effective blood glucose control agent in the absence of other "active components" due to the resultant formation of the inactive quinhydronic structure. In view of this fact, it is speculated that the good results achieved with the compositions of Examples 12 and 13 are due to the fact that sufficient FAD is present to oxidize the inactive quinhydronic form to the active quinonic form, thereby regenerating the desired quinonic form. However, the oxidizing- energizing compositions containing Q10 plus FAD plus other components—not just UTP—can be used when it is desired to combine good oxidative power with very good properties of Q10 as a "dietary fortifying product."

It should be mentioned that the same good results are obtained when the compositions Q10+FAD+GOD or Q10+FAD+ TPN or Q10+FAD+TPN+UTP OR Q10+FAD+TPN+GOD are substituted for the OEC compositions employed in examples 12 and 13. Similarly, when the oxidizing-energizing compositions of Examples 12 and 13 include 10% by weight of one of the optional enzyme components, namely, glucokinase or glucose 6-phosphate dehydrogenase, etc., equivalent blood glucose concentrations may be expected.

The foregoing examples show that the inventive oxidizing energizing compositions potentiate the blood glucose lowering effects of antidiabetic drugs containing a sulfonamide group. Further, the examples disclose that many combinations of coenzymes and GOD enzyme are effective to potentiate said antidiabetic drugs and that the preferred oxidizing energizing compositions provide the lower blood glucose values at the same carbohydrate ingestion level.

This specification has been typed using an IBM computer as a word processor and this machine does not enable the user to use either subscripts or superscripts. Thus, the chemical formulae presented herein are written on a single line without subscripts or superscripts. The representations in the chemical formulae depicted as CH2, CH3, NH2, CH3O, FADH2, etc. refer to the chemical radicals wherein the numbers 2 and 3 appear as subscripts and should be so understood by the reader:

What is claimed is:

1. A non-toxic, oxidizing energizing composition suitable for use as an accelerator of the carbohydrate oxidative degradation metabolic process or of the direct oxidation of glucose which consists essentially of, by weight, (A) 10% to 95% of flavine adenine dinucleotide coenzyme (FAD) and (B) 5% to 90% of a coenzyme or enzyme selected from the group consisting of flavine mononucleotide coenzyme (FMN), ubiquinone coenzyme (UBQ), uridine 5'-triphosphate coenzyme (UTP), triphosphopyridine nucleotide coenzyme (TPN), diphosphopyridine nucleotide coenzyme (DPN), adenosine triphosphate coenzyme (ATP), uridine diphosphate glucose coenzyme (UDPG), guanosine 5'-triphosphate coenzyme (GTP), glucose oxidase enzyme (GOD) and mixtures thereof; and, (C) 0 % to less than 50% of an enzyme selected from the group consisting of fructosediphosphate aldolase, phosphofructokinase, hexokinase, glucokinase, glucose 6-phosphate dehydrogenase, glucose phosphate isomerase, D-glucose-phosphotransferase and mixtures thereof, said composition being effective to reduce the blood glucose concentration in a human body afflicted with diabetes.

2. A composition in accordance with claim 1 wherein component (B) is selected from the group consisting of at least one of 20% to 50% of FMN, 5% to 80% of UBQ, 5% to 40% of UTP, 5% to 70% of TPN, 50% to 80% of ATP, 5% to 20% of UPDG, 25% to 45% of GTP, 5% TO 60% of DPN and 20% to 90% of GOD.

3. A composition in accordance with claim 2 wherein component (B) is selected from the group consisting of at least one of 5% to 40% of UTP, 5% to 70% of TPN, 5% TO 20% UDPG, 20% to 80% of UBQ and 20% to 90% of GOD.

4. A composition in accordance with claim 3 which consists essentially of 60% to 90% of FAD, 5% to 25% of TPN and 5% to 15% of UTP.

5. A composition in accordance with claim 3 which consists essentially of 10% to 30% of FAD, 15% to 30% of TPN and 40% to 70% of GOD.

6. A composition in accordance with claim 3 which consists essentially of 10% to 30% of FAD and 70% to 90% of GOD.

7. A composition in accordance with claim 3 which consists essentially of 30% to 70% of FAD, 20% to 60% of UBQ and 10% to 25% of UTP.

8. A composition in accordance with claim 3 which consists essentially of 30% to 50% of FAD, 15% to 30% of FMN, 20% to 40% of UBQ and 10% to 20% of UTP.

9. A composition in accordance with claim 2 which further includes as an additional ingredient up to 25% by weight of component (C).

10. In combination, 1 mg. to 100 mg. of an oxidizing-energizing composition which consists essentially of, by weight, (A) 10% to 95% of FAD; (B) 5% to 90% of a coenzyme or enzyme selected from the group consisting of FMN, UBQ, UTP, TPN, DPN, ATP, UDPG, GTP, GOD and mixtures thereof; and, (C) 0% to less than 50% of an enzyme selected from the group consisting of fructosediphosphate aldolase, phosphofructokinase, hexokinase, glucokinase, glucose 6-phosphate dehydrogenase, glucose phosphate isomerase, D-glucose-phosphotransferase and mixtures thereof; and either insulin or a sulfonamidic antidiabetic drug in an amount effective to lower the blood glucose concentration in the human body, said concentration of insulin on the sulfonamidic antidiabetic drug being the total daily dosage of said composition and said combination yielding a blood glucose concentration which is lower than the concentration produced by the insulin or the sulfonamidic antidiabetic drug alone.

11. A combination in accordance with claim 10 wherein said sulfonamidic antidiabetic drug is selected from the group consisting of 1.25 mg. to 20 mg. of glyburide, 125 mg. to 750 mg. of chlorpropamide, 250 mg. to 1250 mg. of tolbutamide and 250 mg. to 1250 mg. of tolazamide, said concentrations being the total daily dosage of said sulfonamidic antidiabetic drug.

12. A combination in accordance with claim 11 wherein the total daily dosage of said composition is 5 mg. to 40 mg.

13. A combination in accordance with claim 12 wherein the total daily dosage of said composition is 10 mg. to 25 mg.

14. A combination in accordance with claim 12 wherein said composition consists essentially of 10% to 95% of FAD and at least one coenzyme or enzyme selected from the group consisting of 5% to 40% of UTP, 5% to 70% of TPN, 5% to 20% of UPDG, 20% to 80% of UBQ and 20% to 90% of GOD.

15. A combination in accordance with claim 13 wherein said composition consists essentially of 10% to 95% of FAD and at least one coenzyme or enzyme selected from the group consisting of 5% to 40% of UTP, 5% to 70% of TPN, 5% to 20% of UDPG, 5% to 80% of UBQ and 20% to 90% of GOD.

16. An improved method of lowering the blood glucose concentration in the human body comprising the step of administering 1 mg. to 100 mg. of an oxidizing-energizing composition which consists essentially of, by weight, (A) 10% to 95% of FAD; (B) 5% to 90% of a coenzyme or enzyme selected from the group consisting of FMN, UBQ, UTP, TPN, DPN, ATP, UDPG, GTP, GOD and mixtures thereof; and, (C) 0% to less than 50% of an enzyme selected from the group consisting of fructosediphosphate aldolase, phosphofructokinase, hexokinase, glucokinase, glucose 6-phosphate dehydrogenase, glucose phosphate isomerase, D-glucose-phosphotransferase and mixtures thereof; said composition being effective to reduce the blood glucose concentration in a human body afflicted with diabetes; in combination with the step of administering the daily dosage of insulin or a sulfonamidic antidiabetic drug in an amount effective to lower the blood glucose concentration in a human body afflicted with diabetes, said combination yielding a blood glucose concentration in the body which is lower than the concentration achieved by the insulin or the sulfonamidic antidiabetic drug alone.

17. A method in accordance with claim 16 wherein the sulfonamidic antidiabetic drug is selected from the group consisting of 1.25 mg. to 20 mg. of glyburide, 125 mg. to 750 mg. of chlorpropamide, 250 mg. to 1250 mg. of tolbutamide and 250 mg. to 1250 mg. of tolazamide is administered, said drug concentration being the total daily dosage of said drug.

18. A method in accordance with claim 17 wherein from 5 mg. to 40 mg. of said composition is administered daily.

19. A method in accordance with claim 18 wherein from 10 mg. to 25 mg. of said composition is administered daily.

20. A method in accordance with claim 18 wherein said composition consists essentially of, by weight, 10% to 95% of FAD and at least one coenzyme or enzyme selected from the group consisting of 5% to 40% of UTP, 5% to 70% of TPN, 5% to 20% of UPDG, 5% to 80% of UBQ and 20% to 90% of GOD.

21. A method in accordance with claim 19 wherein said composition consists essentially of, by weight, 10% to 95% of FAD and at least one coenzyme or enzyme selected from the group consisting of 5% to 40% of UTP, 5% to 70% of TPN, 5% to 20% of UPDG, 5% to 80% of UBQ and 20% to 90% of GOD.

* * * * *